United States Patent [19]

Kuderna et al.

[11] 4,062,649

[45] Dec. 13, 1977

[54] DEPLETION INDICATOR FOR CONTROLLED-RELEASE PESTICIDE FORMULATIONS

[75] Inventors: Jerome G. Kuderna; Paul M. Saliman, both of Modesto, Calif.

[73] Assignee: Shell Oil Company, Houston, Tex.

[21] Appl. No.: 464,869

[22] Filed: Apr. 29, 1974

[51] Int. Cl.² ............................................ G01N 31/22
[52] U.S. Cl. .............................. 23/230 R; 23/232 R; 23/253 TP
[58] Field of Search .......... 23/230 R, 253 TP, 232 R; 116/114 AM; 424/219

[56] References Cited

U.S. PATENT DOCUMENTS

| | | | |
|---|---|---|---|
| 2,956,073 | 10/1960 | Whetstone | 424/219 X |
| 3,084,658 | 4/1963 | Schell | 116/114 AM |
| 3,139,328 | 6/1964 | Jacob | 23/253 TP |
| 3,681,027 | 8/1972 | Smith | 23/253 TP |

OTHER PUBLICATIONS

D. F. Heath, Organophosphorus Poisons, Pergamon Press, 1961, pp. 72, 73, 80, 81.

*Primary Examiner*—Robert M. Reese

[57] ABSTRACT

The end of the useful life of a controlled-release formulation containing a volatile phosphate ester pesticide is signalled visually by change in the color of an indicator matrix positioned relative to the formulation so as to contact a representative proportion of the pesticide vapors as they are emitted from the formulation.

4 Claims, No Drawings

DEPLETION INDICATOR FOR CONTROLLED-RELEASE PESTICIDE FORMULATIONS

FIELD OF THE INVENTION

This invention relates to a method for determining the end of the useful life of a controlled-release formulation of a volatile phosphate ester pesticide. More particularly, this invention relates to a method for visually determining when the rate at which a volatile phosphate pesticide is released from a controlled-release formulation thereof falls below the rate needed to control insects in the environment surrounding the formulation.

BACKGROUND OF THE INVENTION

Well known in the art are formulations of volatile phosphate esters which release vapors of the ester slowly at controlled rates to provide sufficient ester in the environment surrounding the formulation to control insects therein over an extended period of time. Examples of such formulations, commonly known as controlled-release formulations, are described in U.S. Pat. Nos. 3,076,744, 3,318,769, 3,169,416 and 3,223,513 and Canadian Pat. Nos. 649,759, 701,470 and 755,683, in which volatile phosphate ester pesticides are formulated in a thermoplastic resin or wax substrate. Other materials, such as thermosetting resins, absorbent papers, clays and other materials have been proposed as the substrate.

In using such formulations to control insects, the formulation is placed in the environment — such as a room or other enclosure — in which the insects are to be controlled. It emits pesticide vapors. A part of those vapors are lost — some being dissipated physically as by loss through open doors or windows or by drafts — and some being lost chemically — the phosphate esters react with moisture in the environment forming products which have little or no pesticidal effect. The formulations are designed to provide more vapors than the amounts that are lost so that in time the formulations provide, and for an extended period maintain in the environment, a pesticide level that effectively kills insects therein. However, typical controlled-release formulations emit the pesticide vapors at a steadily decreasing rate so that eventually the pesticide loss rate exceeds the rate at which the pesticide is emitted form the formulation and the level of pesticide vapor in the environment falls below the concentration needed to control insects therein. This point marks the end of the effective life of the formulation and it is common practice to consider that the pesticide has been depleted from the formulation when this point is reached.

It has been difficult for a householder or other user of such a formulation to know precisely when the useful life of such a formulation has come to an end. First, the "end" comes gradually, and without any apparent change in the appearance of the formulation, or any abrupt change in its properties. Second, since such formulations ordinarily are used under a variety of conditions such as temperature and extent and pattern of air flow about them, etc., and these conditions can change considerably during use, it is difficult to generalize and predict or estimate in any particular case precisely when the "end" will come.

Determination of the "end" is further complicated in the case of such formulations which are associated with means (such as containers) which permit the flow of the pesticide vapors from the formulation to be halted at will — i.e., "on-off" formulations. To enable the user to have some estimate of when the insecticide has been depleted, it is necessary for him to keep an account of the time the formulatiom is "on."

SUMMARY OF THE INVENTION

A method has now been discovered which enables a user of a controlled-release formulation of a volatile phosphate ester pesticide to determine visually when the effective life of the formulation is at an end. The new method measures the useful life of the formulation in terms of the flow of pesticide vapors emitted therefrom. Consequently, it measures the "life" of the formulation only when the pesticide vapors are being emitted (measuring the "on" periods and ignoring the "off" periods in an "on-off" formulation) and to a large extent without regard to the conditions under which the controlled-release pesticide formulation is used.

The new method is based upon two discoveries — the first being that if a mixture of an inorganic base and a color-change indicator for acid-base reactions is placed in the pesticide vapors emitted from a controlled-release formulation of a volatile phosphate ester pesticide, neutralization of the base occurs, eventually leading to change in the color of the indicator from its acid form (indicating pH in the basic range) to its neutral or basic form (indicating neutralization of the base and a pH in the neutral to slightly acid range).

The second discovery is that if the base/indicator mixture is so placed, relative to the pesticide formulation, that it essentially at all times contacts a representative (i.e., aliquot) portion of the emitted vapors, there appears to be an essentially direct (proportional) relationship between the amount of base neutralized and the total amount of pesticide vapors emitted. Since the rate at which pesticide vapors are emitted is known to be related to the total amount of pesticide vapor released, by so positioning the base/indicator mixture, the amount of base in the mixture can be chosen so that the indicator changes color at the time the pesticide formulation reaches the end of its useful life. This relationship has been studied experimentally and found to exist. The mechanism by which the pesticide vapor reacts with the base is not known with certainty; it may react, at least in part, directly with the base but it is believed that the predominant reaction is with moisture in the air (hydrolysis, a known reaction) or in association with the base and/or indicator to form one or more acid phosphate esters, which react with the base, with the base being otherwise inert, or acting as catalyst for the hydrolysis, then reacting with the acid phosphate esters. However, whatever the mechanism involved, these discoveries provide basis for a practical method for ascertaining when the formulation has been depleted of pesticide and has reached the end of its useful life.

Taking, for example, dimethyl 2,2-dichlorovinyl phosphate (DDVP), a typical volatile, pesticidally active phosphate ester: it reacts with water (hydrolysis) including moisture (including water vapor) in air, into two main products

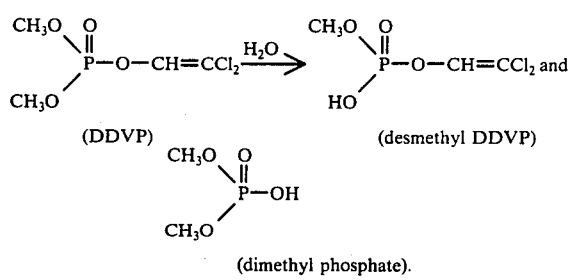

(DDVP)  (desmethyl DDVP)

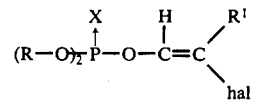

(dimethyl phosphate).

These acidic partial esters readily react with (neutralize) inorganic bases to form the corresponding salts. If a suitable color-change, acid/base indicator is present, it will change color when all of the base has been neutralized. The rate at which DDVP vapors are emitted from a controlled release formulation can be determined by measurement under the expected conditions of use. The vapor emission rate from such formulations has been shown to be related to the amount of pesticide remaining in the formulation (and thus the total amount that has been emitted). By placing a base/indicator mixture at a location with respect to the formulation where it can be contacted and thus reacted with a representative proportion of the emitted pesticide vapors, an amount of base can be chosen so that all of the base will be neutralized (and the indicator thus change color) at the end of the effective life of the formulation. The change in the color of the indicator thus signals the depletion of the DDVP and the end of the effective life of the formulation.

Accordingly, in general terms, the new method is a method of visually determining the end of the effective life of a controlled-release formulation of a volatile phosphate ester pesticide which comprises positioning a mixture of an inorganic base and a color-change indicator for acid/base reactions in a position relative to the formulation where it contacts essentially at all times a representative portion of the pesticide vapors emitted from the formulation, the amount of base being predetermined and directly related to the effective life of the formulation, and ascertaining visually when the color of the indicator changes to the color of its neutral or basic form.

The physical form (i.e., solid or liquid) of the base/indicator mixture is not a critical feature of the invention and is chosen to permit positioning of the mixture at an appropriate position relative to the formulation so that the necessary portion of the vapors can effectively contact the mixture. If a liquid mixture is used, preferably the liquid medium is water or water and a miscible organic liquid suited to formulation of the indicator (these being the solvents customarily used to formulate such indicators). In many, if not most cases, a practical embodiment of such formulations is a solid mixture of the base and indicator impregnated on an absorbent inert carrier, and to enhance absorption of the pesticide vapors and of water vapor (to ensure rapid, complete hydrolysis of the pesticide and reaction with the base/indicator), a humectant.

Thus, a subgeneric aspect of the method of this invention is that wherein the base/indicator mixture is formulated with an absorbent, inert carrier and a humectant.

For convenience together with brevity, but without sacrifice of accuracy, the combination of base and indicator and of base, indicator, humectant and carrier will hereinafter be designated as "depletion indicators." The combination of base, indicator, humectant and carrier form another aspect of the present invention.

These depletion indicators can be used with any controlled-release formulation which emits vapors of a volatile phosphorus ester pesticide. Of such formulations, of particular interest are controlled-release formulations of volatile vinyl phosphate pesticides which can be described by the general formula $$(R-O)_2\overset{X}{\underset{\uparrow}{P}}-O-\underset{\underset{H}{|}}{C}=C\overset{R^1}{\underset{hal}{\diagdown}}$$

wherein R is alkyl of from 1 to 2 carbon atoms, $R^1$ is hydrogen or halogen (preferably middle halogen—that is, chlorine or bromine), hal is halogen (preferably middle halogen) and X is oxygen or sulfur. U.S. Pat. Nos. 2,956,073, 3,318,769 and 3,745,198 disclose such esters, including for example:

dimethyl 2,2-dichlorovinyl phosphate
diethyl 2,2-dichlorovinyl phosphate
dimethyl 2-chlorovinyl phosphate
diethyl 2-chlorovinyl phosphate
dimethyl 2,2-dichlorovinyl thionophosphate
diethyl 2,2-dichlorovinyl thionophosphate
dimethyl 2,2-dibromovinyl phosphate
diethyl 2,2-dibromovinyl phosphate
dimethyl 2-bromovinyl phosphate
diethyl 2-bromovinyl phosphate
dimethyl 2,2-dibromovinyl thionophosphate
diethyl 2,2-dibromovinyl thionophosphate
dimethyl 2-bromovinyl thionophosphate
diethyl 2-bromovinyl thionophosphate Of particular interest are those wherein $R^1$ is H or chlorine, hal is chlorine and X is oxygen. Of most interest because of their widespread use are thermoplastic resin (particularly polyvinyl chloride resin) formulations of DDVP (R = methyl, X = oxygen, $R^1$ = chlorine and hal = chlorine).

Any inorganic base that is non-volatile, stable to moisture and to oxygen in the air is suitable. Suitable bases include the alkali metal and alkaline earth metal hydroxides and carbonates, the alkali metal hydroxides and carbonates being preferred. Because of its ready availability and low cost, sodium hydroxide is most preferred.

As the indicator there can be used any acid-base indicator having a color change between pH4 and pH8. Typical of such indicators are those mentioned at pages 1304-5 of The Merck Index, Eighth Edition, 1968, and including bromcresol purple, bromothymol blue, lacmoid, methyl red, chlorophenol red, bromphenol red, bromcresol green and the like. Particularly suuitable are methyl red and mixtures of methyl red and bromothymol blue. The amount of the indicator used will follow conventional practice in the use of such indicators in following acid/base reactions. Generally, the amount is dictated by the depth of color to be attained in the depletion indicator to provide ready, accurate visual determination when the pesticide formulation has reached the end of its useful life.

Liquid base/indicator combinations can be used if means are used to contact such a combination constantly with the needed proportion of the pesticide vapors. Suitable liquid vehicles include water and water and water-miscible organic liquids conventionally used with such indicators. The concentration of base and indicator in the liquid are not known to be critical.

In a preferred embodiment of the invention, the base-/indicator mixture is supported by an absorbent inert solid carrier. While other materials having these characteristics would be satisfactory, paper appears to be suitable and most convenient in ordinary use. The paper that is used must be free of any material such as a glaze, filler, or other material conventionally added to paper that would interfere with absorption of the pesticide (including reacting with the pesticide), reaction of the pesticide with the base, or chemically or physicaly interfering or masking the color change of the indicator. Paper of the kind and quality of filter paper appears to be most suitable.

Since the hydrolysis of the phosphate pesticide appears to be primarily dependent upon the presence of moisture in the base/indicator combination and the humidity in and around the pesticide formula can vary considerably during use, it is preferred to include a humectant in the base/indicator and base/indicator/-carrier combinations. This additive acts to insure the presence of moisture in the combination and helps to maintain the amount of moisture therein at a constant level. Any of the materials commonly used as humectants are suitable, the polyhydric alcohols apparently being most useful for the purpose: Clark & Hawley, "The Encyclopedia of Chemistry," Reinhold Publishing Co., N.Y. 1957, page 475. Examples include glycerol, propylene glycols, sorbitol, pentamethylene glycol, α-methylglycerol, β-methylglycerol monochlorohydrin and polyethylene glycols. Also apparently suitable are the N-hydroxylactamides.

Within certain limits, the amount of humectant employed is not critical; in general sufficient should be used to provide the necessary hygroscopicity to the depletion indicator combination. Too much will cause the depletion indicator to be wet, and its effectiveness reduced; too little will result in a depletion indicator that may be too dry and does not contain enough moisture to insure rapid and complete hydrolysis of the pesticide vapors. (Also, such a dry formulation may not readily absorb the acid phosphate esters.) The amount of humectant used suitably can vary from about the weight of the base used to about ten times that amount. In most cases, a humectant/base weight ratio of from about three to about eight will be found to be satisfactory.

As has already been indicated, the amount of base used is determined by the amount of pesticide to be absorbed by the depletion indicator during use of the pesticide formulation. The amount of pesticide to be absorbed will depend upon the area of the base/indicator matrix exposed to the pesticide vapors and upon the location of the matrix relative to the pesticide formulation. The area of the matrix so exposed is not critical within two limits: it must be large enough for the color change to be readily apparent, but it must not be so large as to interfere with free emission of the pesticide vapors. To ensure consistent results, it usually will be found desirable to position the indicator matrix close to the pesticide formulation. The matrix must not touch the surface of the formulation for erroneous results could be obtained because of direct transfer of pesticide from the surface of the formulation to the matrix. Usually, it will be found desirable to position the matrix from one millimeter to one centimeter from the surface of the formulation. Otherwise, the matrix can be located in any position from which it can be inspected readily. Because of the variables involved — the shape and size of the pesticide formulation, the conditions under which it will be used and the size and location of the indicator matrix are some of the more significant factors — generally, the amount of base used will have to be determined empirically, taking into account the various factors discussed herein. It is preferable that the amount of base to be used be confirmed experimentally before actual use.

The preferred solid depletion indicators can be prepared by making a solution or suspension of the base, the indicator and the humectant in water or other suitable liquids as described hereinbefore, then applying it to the carrier and letting it dry to equilibrium. Because of the humectant, a part of the water will be retained and this, plus any water that the depletion indicator may absorb from the air when at equilibriium or during use of the pesticide formulation, will be sufficient to hydrolyze pesticide absorbed by the depletion indicator.

The depletion indicator can be physically of any suitable form (a) that is adapted to being positioned in the appropriate location relative to the pesticide formulation, and (b) that can be visually inspected readily. Thus, the depletion indicator could take the form of a paper tab all or partially impregnated with the base/indicator/humectant combination affixed to the pesticide formulation, or a holder therefor, in such a way as to position the impregnated portion at the appropriate location relative to the pesticidal formulation. The depletion indicator also could take the form of a piece of white paper impregnated with the base/indicator/-humectant combination so as to form a spot in the paper — such a technique could be advantageous since it would enable contrast of the color of the indicator when it changes color against the white background. Of course, colored paper could be used if the color were one that would emphasize the color of the basic form of the indicator. In fact, since under the conditions of use as contemplated by this invention the color of the basic form of the indicator may not be vivid, and the indicator may not change color suddenly, but may pass through intermediate colors, it may be desirable for comparison to locate on or near the paper bearing the basic/indicator/humectant combination, a spot or spots of the base/indicator/humectant combination in which the base has been neutralized and the indicator is in the basic form. This will inform the user of the pesticidal formulation of the color the base/indicator/humectant depletion indicator will become at the time the pesticidal formulation has come to the end of its useful life and will permit side-by-side comparison of the color to insure that in fact the correct color, indicating depletion of the pesticide, has been attained. Also, two or more depletion indicator spots can be used — one or more in which the amount of base is materially less than that required for signalling depletion of the pesticide so that one spot changes to the basic form and color of the indicator providing the reference color for comparison. If desired, a series of such spots can be used containing specified, increasing amounts of base up to that which will signal depletion of the pesticide; as each spot changes color, the consumer will have an indication of the length of this remaining useful life of the pesticide formulation. When applying the base/indicator/-humectant combination to the paper, the area of paper to which it is applied can be restricted to a desired area by application prior to application of the indicator combination of a wax, or other water-insoluble material that will penetrate the paper barrier — as by treating the appropriate portions of the paper with a solution of the wax in a volatile solvent such as cyclohexane, or a solution of the other material in a suitable volatile solvent, then allowing the solvent to evaporate before applying the indicator/base/humectant combination. The wax or other material prevents the indicator solution from migrating outside the contemplated area. The base/indicator/humectant combination can be applied as a solution in water, then allowing the solution to dry to equilibrium with its surroundings.

The character and practice of this method of the invention is illustrated in the following examples:

EXAMPLE 1

On pieces of filter paper, 3 cm × 2 cm, was drawn the outline of three squares, 1.3 cm per side, using a solution of 2 g of paraffin wax in 10ml of cyclohexane. The papers then were heated for 10 minutes at 100°–110° C, at which conditions the cyclohexane evaporated and the wax spread out to define the outline of three squares on each piece of paper, each having an area of 1 cm².

Two indicator solutions were prepared: Solution No. 1: 0.3N sodium hydroxide in water containing 1 mg of methyl red indicator and 50 mg of glycerine per milliliter of the solution. Solution No. 2: 0.05N sodium hydroxide in water containing 1 mg of methyl red indicator and 50 mg of glycerine per milliliter of the solution.

Onto the middle square on each piece of paper was applied 20 microliters of Solution No. 1 while 20 microliters of Solution No. 2 was applied to each of the two outer squares on each piece of paper. The treated papers then were dried.

Each treated paper was placed 0.5 cm from a commercial slow-release pesticide strip having an expected useful life of about 90 days under the expected conditions. These strips contained approximately 20% of dimethyl 2,2-dichlorovinyl phosphate (conveniently and hereinafter designated as DDVP) as the pesticide (insecticide), the remainder being plasticized polyvinyl chloride.

The strips and associated indicator papers were hung in various locations and observations of the indicator papers were made periodically. The indicator patches originally were yellow in color. After 14 days, the outer patches were pink in color, the center patches were still yellow. After 40 days the outer patches were red in color and the central patches were beginning to change color; they matched the color of the outer patches after about 100 days. The average variation in the time required for the colors to match, among the various strips, was ± 15 days.

EXAMPLE 2

A variation of the procedure described in Example 1 was utilized. Using sodium hydroxide solutions of increasing concentration and constant amounts of indicator and humectant, 10 microliters of each solution were applied to a series of wax bounded squares arranged vertically in the pieces of paper with the solution having the lowest concentration of sodium hydroxide being applied on the square at the bottom and the solution having the highest concentration of sodium hydroxide being applied on the square at the top of the row.

The treated pieces of paper were treated as in Example 1. As time passed, the squares changed color from yellow to red, in succession from the bottom, upward, thus indicating the amount of DDVP released and the end of the useful life of each strip.

Other bases that have been used and found to be satisfactory are: sodium carbonate, potassium carbonate, magnesium hydroxide, potassium hydroxide, calcium hydroxide and calcium carbonate.

Other indicators that have been used include: lacmoid, congo red, bromcresol purple, guinea green, 2-(p-dimethylaminophenylazo)pyridine and combinations of these.

We claim as our invention:
1. A method for visually determining the end of the effective life of a controlled-release formulation of a volatile phosphate ester pesticide of the formula

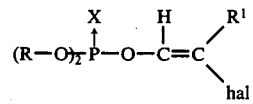

wherein each R is alkyl of from 1 to 4 carbon atoms, $R^1$ is hydrogen, chlorine or bromine, hal is chlorine or bromine and X is oxygen or sulfur, which method comprises positioning a mixture of an inorganic base, a color-change indicator for acid/base reactions, an inert, absorbent carrier and a humectant, in a position relative to the formulation where it contacts essentially at all times a representative proportion of the pesticide vapors emitted from the formulation, the amount of base being predetermined, and directly related to, the effective life of the formulation, and ascertaining visually when the color of the indicator changes to the color of its neutral or basic form.

2. A method according to claim 1 wherein the carrier is paper.

3. A method according to claim 2 wherein, referring to the phosphate ester pesticide, halogen present is middle halogen.

4. A method according to claim 3 wherein, referring to the phosphate ester pesticide, both of R are methyl, X is oxygen, $R^1$ is chlorine and hal is chlorine.

* * * * *